United States Patent [19]
Kouchi et al.

[11] Patent Number: 5,741,213
[45] Date of Patent: Apr. 21, 1998

[54] APPARATUS FOR ANALYZING BLOOD

[75] Inventors: Yasuhiro Kouchi; Kaoru Asano, both of Kobe; Ken Ishihara, Takarazuka, all of Japan

[73] Assignee: Toa Medical Electronics Co., Ltd., Hyogo, Japan

[21] Appl. No.: 736,822

[22] Filed: Oct. 25, 1996

[30] Foreign Application Priority Data

Oct. 25, 1995 [JP] Japan ................. 7-302088

[51] Int. Cl.⁶ .................. A61B 5/00; G06K 9/00
[52] U.S. Cl. .................. 600/310; 600/407; 382/134; 356/39
[58] Field of Search .................. 600/309, 310, 600/322, 476, 473, 479, 407; 356/39; 382/128, 133, 134, 199

[56] References Cited

U.S. PATENT DOCUMENTS

| | | |
|---|---|---|
| 4,998,533 | 3/1991 | Winkelman . |
| 5,099,521 | 3/1992 | Kosaka ................. 382/133 |
| 5,459,636 | 10/1995 | Gee et al. ................. 382/199 |
| 5,579,415 | 11/1996 | Takano et al. ................. 382/199 |
| 5,598,842 | 2/1997 | Ishihara et al. . |

FOREIGN PATENT DOCUMENTS 4-161915   6/1992   Japan .

*Primary Examiner*—Jennifer Bahr
*Assistant Examiner*—Eric F. Winakur

[57] ABSTRACT

An apparatus for analyzing blood includes an image capturing device for capturing an image including at least one object blood cell and an analyzer for analyzing the captured image as an image $F(x, y)$ in an x-y coordinate system. The analyzer includes an edge calculator for calculating an edge intensity distribution $E(x, y)$ representing an outline of the image $F(x, y)$; a weight memory for storing in advance a weight distribution $W(i, j)$ corresponding to an average outline of the object cell; an assessment value calculator for obtaining an assessment value $C(x, y)$ at each point $(x, y)$ by calculating a degree of correspondence between the edge intensity distribution $E(x, y)$ and the weight distribution $W(i, j)$ for each point $(x, y)$; and an extractor for extracting a point $(x, y)$ at which the assessment value $C(x, y)$ is larger than a predetermined value, thereby determining that the object blood cell is present at the point $(x, y)$. The apparatus is useful as a device for identifying the object blood cell.

12 Claims, 13 Drawing Sheets

▨ 1.0

▦ 0.5

☐ 0.25

(a)

(b)

(d)

(c)

1.0

0.5

0.25

0.125

APPARATUS FOR ANALYZING BLOOD

BACKGROUND OF THE INVENTION

1. Field of the Invention

The present invention relates to an apparatus for analyzing blood. More particularly, the present invention relates to an apparatus for optically measuring a blood sample for identification of the blood cell components required in blood test.

2. Description of the Related Arts

Hematological inspection items such as number of blood cells (number of leukocytes, number of erythrocytes, number of thrombocytes, etc.), hematocrit value, hemoglobin amount, and red blood cell indices mean corpuscular volume: MCV, mean corpuscular hemoglobin HCH, mean corpuscular hemoglobin concentration: MCHC) that are obtained by analyzing a blood sample are extremely important for diagnosis, treatment, and the like and are items that are most frequently counted by measurement in clinical inspection.

Generally, such a hematology test involves collecting blood from a living body to analyze a sample thereof with an analyzer. However, the collection of blood from the living body causes considerable pain to the living body. Also, since the collected blood is usually transported, before analysis, to an inspection room where an analyzing apparatus is placed, it is impossible to conduct a real-time hematology test during diagnosis. Moreover, the above method is always accompanied by a fear that needles for blood collection might cause an accident due to erroneous injection when they are used for collecting blood from a different living body infected with an infectious disease such as hepatitis and AIDS.

Thus, a demand has been made for many years that an apparatus be developed that allows practitioners to perform a blood test in a non-invasive manner. When such a blood analyzer is installed beside the bed on which the living body is laid, the practitioners can monitor real-time conditions thereof on the spot without difficulty.

One of the conventionally known apparatus used for such hematological inspection is disclosed in "Apparatus and method for in vivo analysis of red and white blood cell indices"(J. W. Winkleman, U.S. Pat. No. 4,998,533) which employs counting the indices of erythrocytes and the number of leukocytes by extracting erythrocytes and leukocytes from images captured with a modified slit lamp.

Also, as a related technique, there is known a video microscope for periodically capturing video images by applying light to an observation site on a surface of a living body so as to observe the bloodstream (See, for example, Japanese Unexamined Patent Publication No. Hei 4 (1992) -161915).

However, the aforementioned U.S. Pat. No. 4,998,533 discloses nothing about specific methods for automatically identifying leukocytes.

When a blood flowing through a blood vessel in a living body is observed by eye inspection with the above apparatus or a video microscope, it is possible to identify spherical and transparent substances capable of being identified as leukocytes flowing therethrough. This seems to be due to the fact that, since the leukocytes are flowing, the periphery of the leukocytes is emphasized against the stationary background for identification.

However, when still images of leukocytes are observed, it is difficult to capture clear images of the leukocytes as particles since the optical difference of the leukocytes against the background is extremely small.

Also, since an image blur is generated by body movement, it is further difficult to identify leukocytes without misidentification. No disclosure on this point is found in U.S. Pat. No. 4,998,533. Moreover, since the video microscope is designed basically for observation by eye inspection, it is difficult to carry out a quantitative analysis of leukocytes, especially an analysis of the number of leukocytes, On the other hand, a simple and general method for identifying particles and cells from these images employs template matching.

However, since the leukocytes flowing within a living body varies in size and are deformed in the flowing direction the method employing the template matching produces poor identification ratio with respect to the leukocytes flowing within the living body or otherwise, an extremely large number of templates must be prepared for their identification, rendering it difficult to conduct a real-time measurement.

Our copending application Ser. No. 08/296,897 describes a non-invasive blood analyzer which calculates the number of leukocytes per unit volume by recognizing leukocytes in images of a region in a blood vessel, but does not teach how to recognize the leukocytes.

SUMMARY OF THE INVENTION

The present invention has been made in view of these circumstances and the purpose thereof is to provide an apparatus for capturing images of blood cells moving through a blood vessel within a living body so as to identify the blood cells, especially the leukocytes, based on the captured images in real-time without being affected by artifacts due to the movement of the body or the like.

Accordingly, the present invention provides an apparatus for analyzing blood comprising: image capturing means for capturing an image including at least one object blood cell and analysis means for analyzing the captured image as an image $F(x, y)$ in an x-y coordinate system, the analysis means including: edge calculation means for calculating an edge intensity distribution $E(x, y)$ representing an outline of the image $F(x, y)$; weight storage means for storing in advance a weight distribution $W(i, j)$ corresponding to an average outline of the object blood cell; assessment value calculation means for obtaining an assessment value $C(x, y)$ at each point $(x, y)$ by calculating a degree of correspondence between the edge intensity distribution $E(x,y)$ and the weight distribution $W(i, j)$ for each point $(x, y)$; and extraction means for extracting a point $(x, y)$ at which the assessment value $C(x, y)$ is larger than a predetermined value, thereby determining that the object blood cell is present at the point $(x, y)$, so that the object blood cell is identified.

DETAILED DESCRIPTION OF THE PREFERRED EMBODIMENTS

Figure 1:
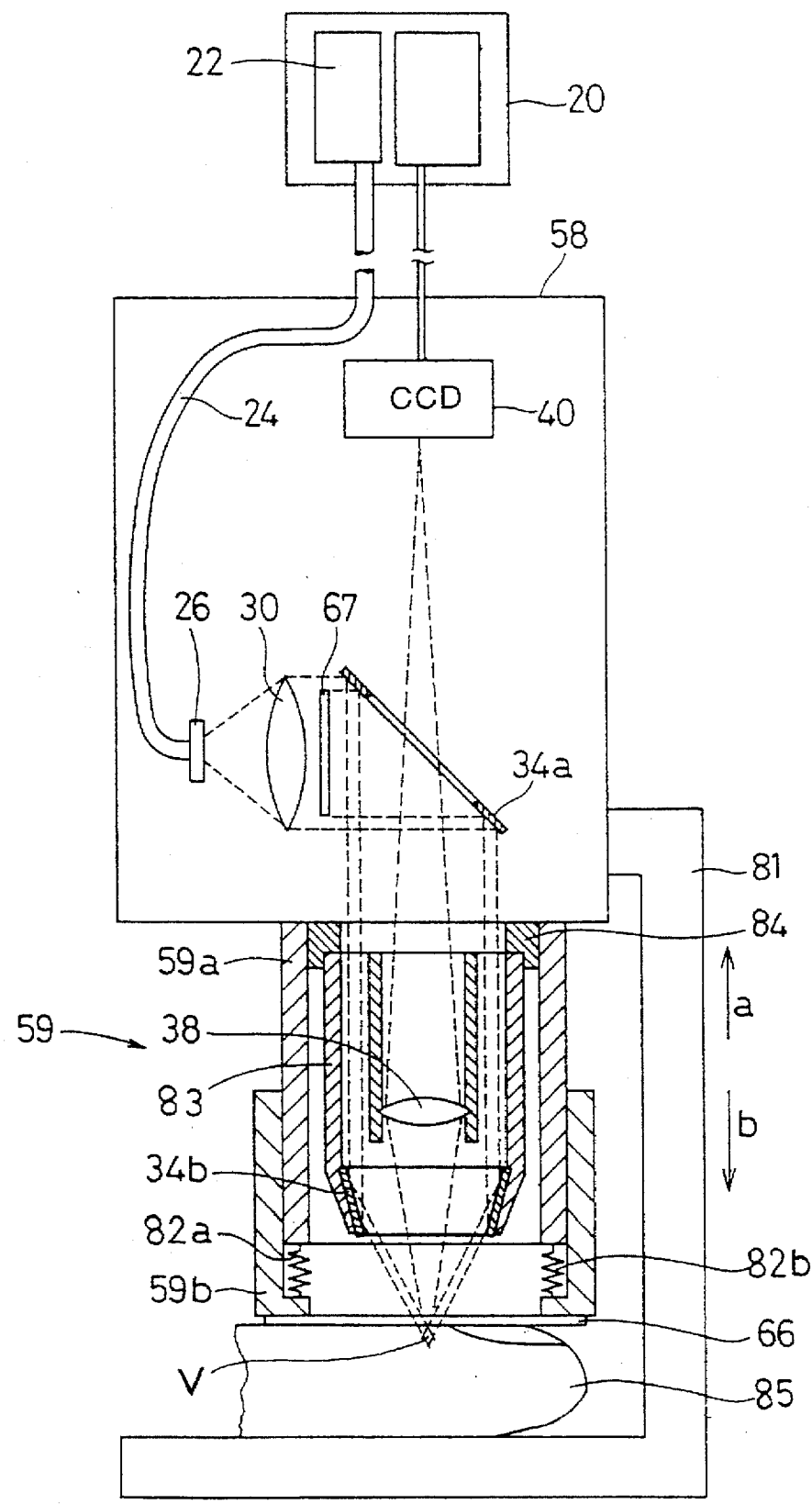
FIG. 1 is an explanatory view for showing the construction of an analyzing apparatus according to an embodiment of the present invention.

The apparatus for analyzing blood according to the present invention is characterized by analyzing blood within a living body in a non-invasive manner. Preferably, the living body is that of mammals including human beings.

It is preferable that the apparatus according to the present invention further includes fixing means for relatively fixing the living body and the image capturing means so that the image capturing means may be fixed on a surface of the living body corresponding to a desired detection region.

The image capturing means according to the present invention includes, for example, an illuminator and an imaging device, the illuminator serving to illuminate a detection re ion including a blood vessel of the living body, and the imaging device serving to sequentially capture images of the illuminated detection region. Here, the term "detection region" recited with reference to the light application means for illuminating the detection region including the blood vessel of the living body is a portion having a blood vessel under its skin, namely a region such as in a lip, a finger, a thumb, or an earlobe including a blood vessel that is present as it is in a living body. The "detection region" does not represent a portion of the living body that has been surgically taken out of the living body. Therefore, it is necessary that the fixing means can fix the image capturing means relative to a portion of the living body. Therefore, it is necessary that the fixing means can fix image campturing means relative to a portion of the living body such as a lip, a finger, a thumb, or on earlobe. Moreover, although the width of the blood vessel included in the detection region is not specifically limited, the blood vessel is preferably a capillary vessel, a venule, or an arteriole which lies near the skin so that good reproducibility may be obtained. Here, blood cell information obtained from the capillary vessel, the venule, or the arteriole may be converted into information of wide blood vessels (middle and large veins and arteries).

As the illuminator of the present invention, either a continuous light source for continuously applying light such as a laser, a halogen lamp, or a tungsten lamp or an intermittent light source for intermittently applying light such as a pulse laser (for example, 7000 series manufactured by Spectra-Physics Co., Ltd.) or a multi-stroboscope (for example, DSX series manufactured by Sugawara Laboratories, Inc., Japan) may be used.

As the imaging device of the present invention, a general CCD imaging element may for example be used The imaging device may include an optical fiber various kinds of reflecting mirrors, a polarizing element, various kinds of lenses, a prism, a slit, or a filter in an optical system for directing the light reflected from the detection region to the CCD imaging element. If the light reflected from the detection region is weak, it is preferable that the imaging device includes an image intensifier. Also, the image capturing means may include polarizing means for removing the unnecessary light components scattered from the detection region.

Further, the imaging device preferably includes a video signal processing circuit for supplying a scanning signal to the CCD imaging element and for processing the outputs from each pixel of the CCD imaging element as a video signal in the signal processing system. Also, the imaging device preferably includes a VTR or a laser disk recorder for recording the video signal.

Alternatively, a commercially available video microscope system can be used as the illuminator and the imaging device.

As the analysis means, a computer for image processing (for example, Quadra 800 manufactured by Apple Computer Corp.) may be used. Further, an analog pre-preprocessor (for example, HK-7000 manufactured by Minolta Co., Ltd. in Japan) may be used in combination so as to adjust the contrast of the captured image signal.

According to the present invention, the assessment calculation means calculates the assessment value C(x, y) at the point (x, y) by the following equation:

$$C(x,y) = \sum_i \sum_j E(x+i, y+j) W(i,j).$$

where the right hand side of the above equation represents a sum of products of the edge intensity distribution and the weight distribution when the two distributions are overlapped with each other so that the point (x, y) in the edge intensity distribution corresponds to the point (0, 0) in the weight distribution.

Since leukocytes have a generally annular outline, the weight distribution W(i, j) is preferably an annular distribution bution data corresponding to the outline of the object blood cells.

In order to differentiate leukocytes from the artifacts, the edge calculation means preferably calculates the edge intensity distributions El(x, y), E2(x, y), ... En(x, y) corresponding to n different directions radiating from a point (x, y), the weight storage means preferably stores the weight distributions W1(i, j), W2(i, j), ... Wn(i, j) corresponding to the n different directions, and the assessment value calculation means preferably calculates the assessment value by summing up the assessment values Cl(x, y), C2(x, y), ... Cn(x, y) calculated corresponding to the n different directions.

Here, each of the weight distributions W1(i, j), W2(i, j), ... Wn(i, j) is preferably a portion of an annular distribution data corresponding to the outline of the object blood cells.

Further, the weight distribution W(i, j) may be calculated based on data obtained by summing up the edges extracted beforehand from a plurality of images of the object blood cells with the edge calculation means.

Also, the present invention can provide an apparatus for analyzing blood wherein the image capturing means comprises an illuminator and an imaging device the illuminator serving to illuminate a detection region including a blood vessel within a living body and the imaging device serving to sequentially capture images of the illuminated detection region, and wherein the analysis means further includes differential image creating means that creates a reference image using at least one of the sequentially captured images of the same detection region and, assuming another of the captured images to be an object image, creates a differential image by taking a difference between the object image and the reference image, whereby the image F(x, y) is defined by the differential image.

Here, the analysis means may further comprise digitizing means for digitizing the reference image and the object image, whereby the differential image is defined by a difference between the digitized reference image and the digitized object image.

Further, the analysis means may comprise a neural network including the edge calculation means, the weight storage means, the assessment value calculation means, and the extraction means. The neural network may receive the image F(x, y) into its input layer and output the extraction m result of the object blood cells from its output layer.

EXAMPLES

The present invention will hereinafter be detailed in conjunction with the embodiments shown by the accompanying drawings. These embodiments and the drawings are not to be construed as being intended to limit the scope of the present invention.

Figure 2:
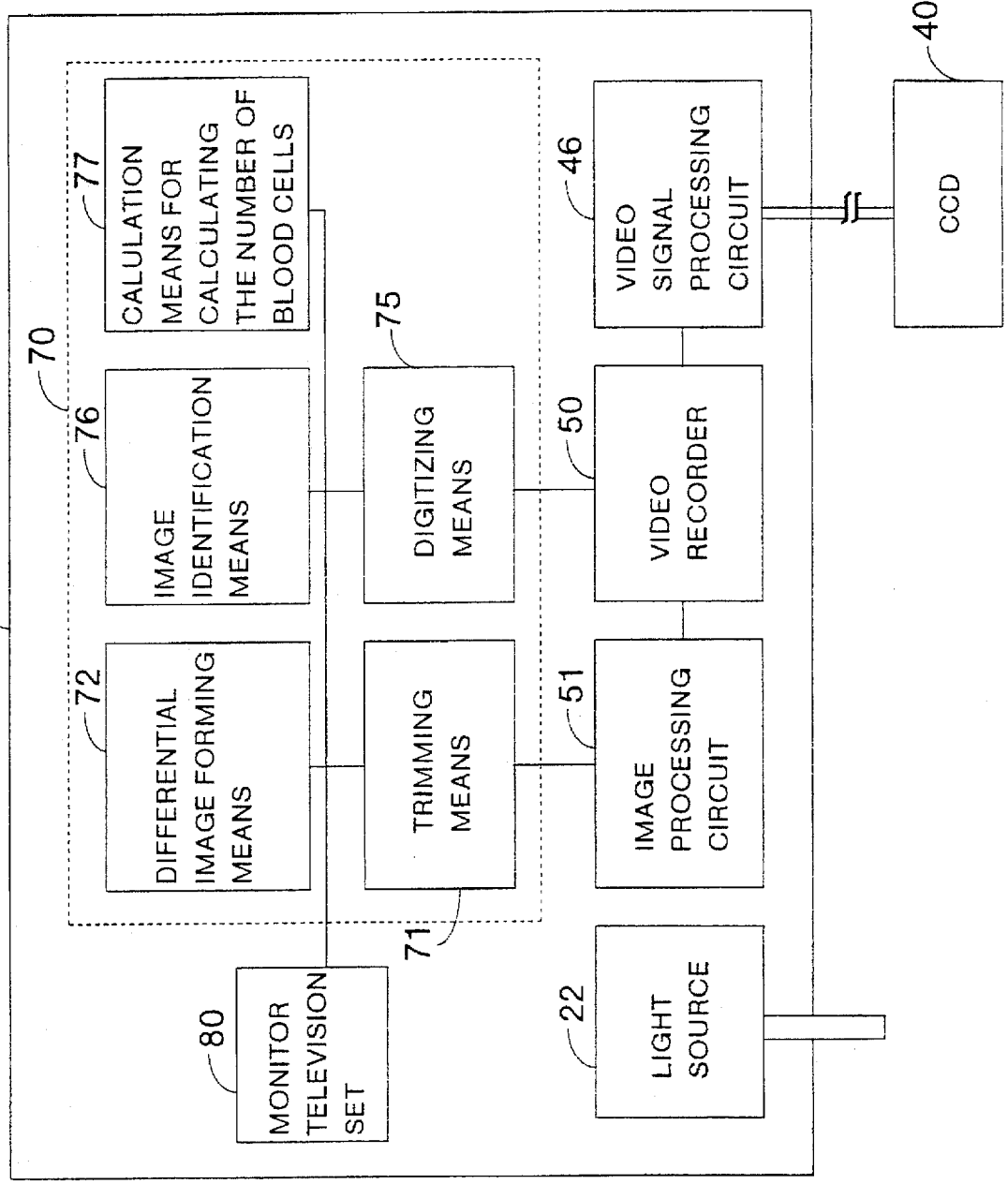
FIG. 2 is an explanatory view for showing the construction of the essential part of FIG. 1.

FIG. 1 is an explanatory view for showing the construction of an analyzing apparatus according to the present invention. FIG. 2 the analyzing apparatus includes image capturing means, fixing means and analysis means, is an explanatory view for showing the construction of a main body portion of the analyzing apparatus shown in FIG. 1.

First, the image capturing means includes an illuminator and an imaging device, the illuminator serving to illuminate a region in a portion of the living body including a blood vessel, and the imaging device serving to capture images of the illuminated region in the following manner.

Referring to FIG. 1 light emitted from the light source 22 in the main body 20 of the analyzing apparatus is led into the probe 58 through the optical fiber 24 to irradiate the diffuser 26. The light is diffused by the diffuser 26 and converted into parallel light by the collimator lens 30.

The central portion of the collimated light is shielded by a disk-like shield 67, whereas the periphery of the collimated light is directed to the outside from the tip 59 of the probe 58 via ring-like mirrors 34a and 34b. Light directed from the tip 59 of the probe 58 toward the nail wall of the finger 85 irradiates the detection region V in the blood vessel via the transparent plate 66 and the skin surface. The light reflected from the detection region V is received by the CCD 40 via the transparent plate 66 and an object lens 38. The main body 20 of the analyzing apparatus analyzes an image captured by the CCD 40.

Here the detection reion V is illuminated with an ultrail-lumination (namely, a dark-field illumination) so that the contrast of captured images may be improved. The dark-field illumination refers to an illumination mode by which the illumination light is directed to the detection region V from the outside of the object lens 38. In other words, the illumination light illuminates the detection region V at an angle broader than an aperture angle of the object lens 38 relative to the detection region V. Consequently, the illumination light reflected at the skin surface is directed to the outside of the object lens 38 and does not reach the CCD 40, so that the contrast of the images captured by the CCD 40 is greatly improved.

Further, the fixing means fixes the image capturing means relative to a portion of the living body in the following manner.

FIG. 1 shows a state in which the probe 58 and part of the subject (finger nail wall) are relatively fixed. An L-shaped support base 81 is attached to the probe 58. The tip 59 of the probe 58 includes a cylinder 59a extending from the probe 58, and a sliding cylinder 59b attached on the external circumference of the end of the cylinder 59a. The sliding cylinder 59b can slide in the directions of arrows a and b. The transparent plate 66 is fixed to the end of the sliding cylinder 59b.

Springs 82a, 82b are provided on the end of the cylinder 59a and urge the sliding cylinder 59b in the direction of the arrow b. An internal cylinder 83 incorporates the object lens 38 and the ring-like mirror 3 4b and is fixed to the probe 58 via a micro-motion element 84. Here, the support base 81, the cylinder 59a, the sliding cylinder 59b, the springs 82a, 82b, and the transparent plate 66 constitute fixing means, while the sliding cylinder 59b, the springs 82a, 82b, and the transparent plate 66 constitute stabilizing means.

When a finger 85 of the subject is inserted between the support base 81 and the transparent plate 66, the springs 82a, 82b press the transparent plate 66 on the nail wall of the finger 85 at an appropriate pressure. The detection region V in the blood vessel of the nail wall is fixed in the sight of the CCD 40, thereby preventing a blur of the detection region V caused by fine vibration of the finger 85.

In addition, the focus of the CCD 40 can be adjusted by moving the lens 38 in the direction of the optical axis (in the direction shown by arrow a or b) with the micro-motion element 84. As the micro-motion element 84, for example, an element with a piezo element P-720 /P-721 (manufactured by Physik Instrumente), or an element with an ultrasonic motor can be used.

The transparent plate 66 is detachably attached on the tip 59 of the probe 58 so that the plate 66 can be replaced for each subject. The transparent plate 66 is replaced for hygienic reasons, i.e., for protecting subjects from contracting diseases.

A glass plate a resin-made flexible film or the like may be used as the transparent plate 66.

Alternatively, the transparent plate 66 itself may not be replaced, and a replaceable film may be placed in close contact with the finger 85.

Furthermore, a liquid or gelatinous optical medium which is safe for the living body is more preferably intervened between the skin surface and the transparent plate 66 in order to prevent irregular reflection of the illuminating light from the skin surface and to obtain a sharp image of the detection region V.

As the optical medium, oil or cream may be used. In this embodiment, a transparent plate is used as the plate 66 contacting the living body. Instead of the plate 66, however, an opaque plate with a light transmitting hole (light passageway) at a central portion thereof may be used, since the blurring of the detection region V can be prevented even with the opaque plate.

In this Example, the detection region is provided in a finger nail wall. However, if the detection region is to be provided in another site such as a lip or an earlobe, it is necessary to use a suitable fixing means corresponding to the site.

Next, the analysis means will be hereinafter explained.

Image signal outputs from each pixel of the CCD 40 are processed by a video signal processing circuit 46, as shown in FIG. 2. Then the video signal processing circuit 46 consecutively forms one frame of image every one thirtieth of a second. The frame images thus formed are sequentially recorded by a video recorder 50 (for example, a laser disk recorder).

The reference numeral 51 represents an image processing circuit, for example, an analog pro-preprocessor HK-7000 (manufactured by Minolta Co., Ltd. in Japan) for adjusting the contrast of the images. The reference numeral 70 represents analyzing means for analyzing the number of blood cells in a blood vessel lying in the detection region V by processing a captured image. As the analyzing means, a device including an image processing computer Quadra 800 (manufactured by Apple Computer Corp.) and a video capture board IQ-V 50 (manufactured by Hamamatsu Photonics Co., Ltd. in Japan) disposed prior thereto may, for example, be used.

The analyzing means 70 includes: trimming means 71 for trimming and outputting a predetermined region of an image frame outputted by the image processing circuit 51; digitizing means 75 for digitizing the images outputted by the trimming means 71; differential image forming means 72 for calculating a difference of pixel data between the digitized images of consecutive frames, thereby forming a differential image having the difference as a pixel data; image identification means 76 for identifying the kind and the position of the blood cell based on the differential image; and calculation means 77 for calculating the number of blood cells per unit volume based on the blood cell images identified during a predetermined period of time. A monitor television set 80 monitors each image formed in the analyzing means 70.

The procedure for identifying leukocytes by using the above analyzing means 70 will be described hereinbelow.

Here, the analyzing means 70 performs image processing by reading out in time series a plurality of frames recorded in the video recorder 50.

Figure 3:
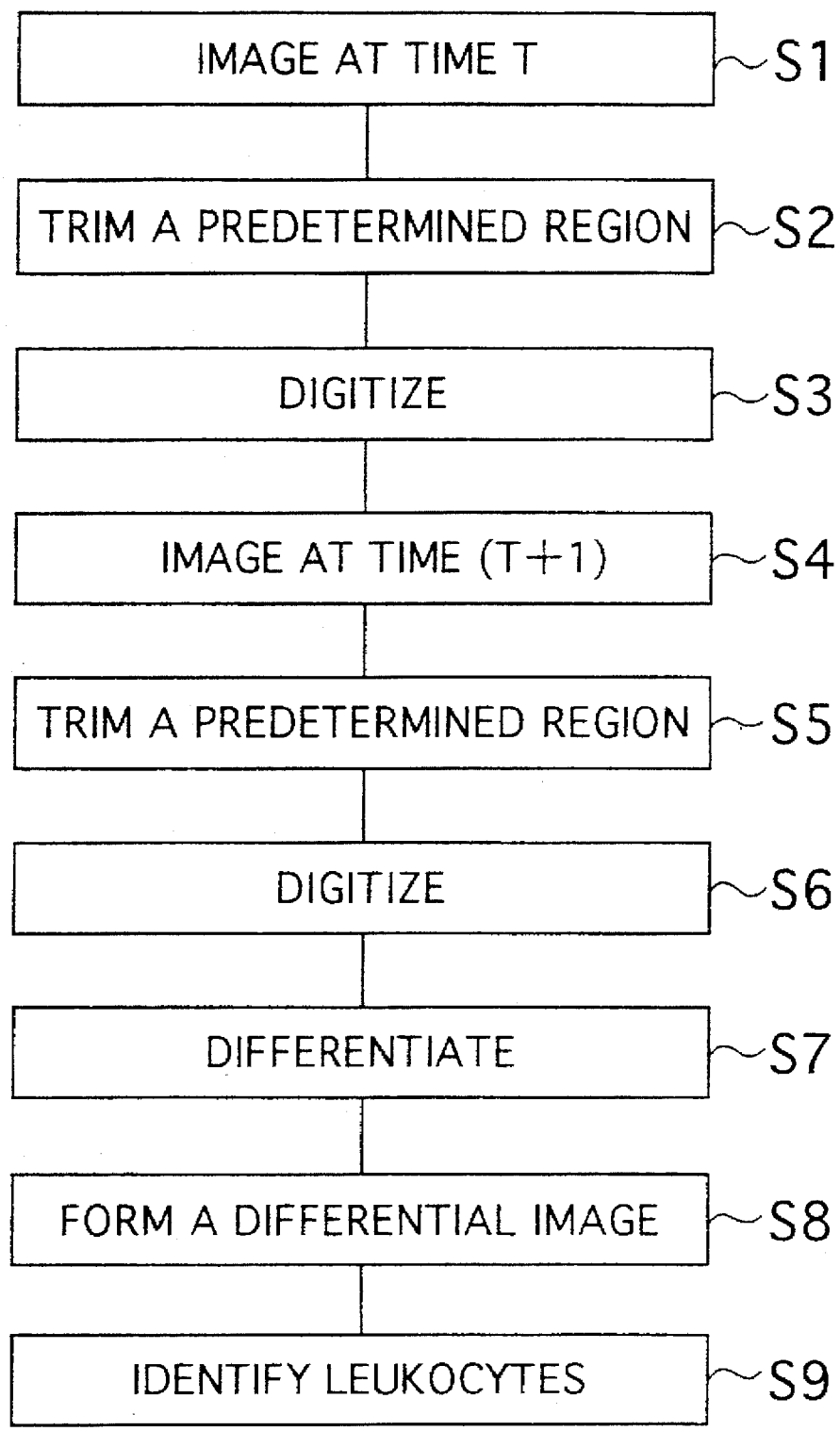
FIG. 3 is a flow chart for showing the operation of the embodiment of the present invention.

As shown in the flow chart of FIG. 3, the frame image at the time t is read out (step S1), and an image of a region including a blood vessel is trimmed as a reference image and digitized (steps S2, S3). Subsequently, the frame image at the time (t+1) is read out (step S4) and an image of the same region as above is trimmed as an object image and digitized (step S5 S6)

Difference of the pixel data between the two digitized images is then calculated (step S?), and a differential image F(x, y) having the difference as a pixel data is formed (step S8). A blood image is detected from the differential image F(x, y), and leukocytes are identified based on the detected blood image (step S9).

The function of identifying the leukocytes in step S9 will be detailed hereinbelow.

Figure 8:
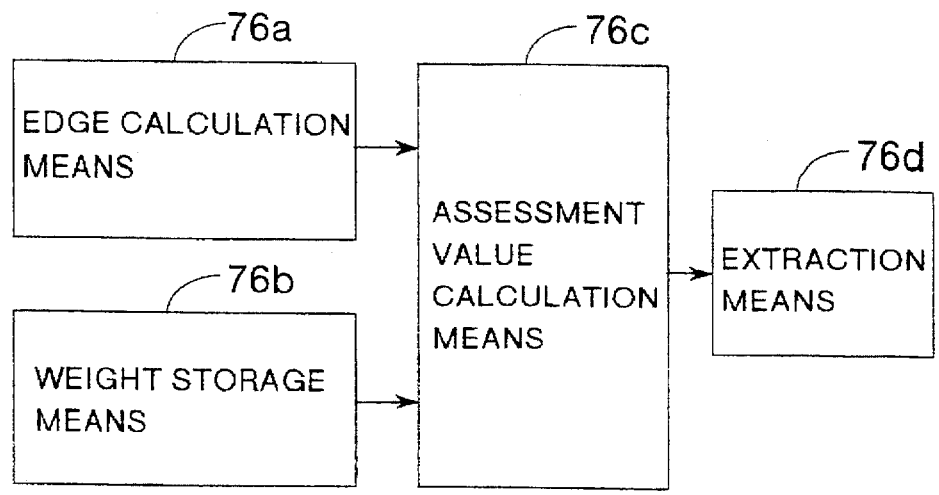
FIG. 8 is a block diagram for showing the construction of an essential part according to the embodiment of the present invention.

Referring to FIG. 8, the image identification means 76 includes: edge calculation means 76a for calculating an edge intensity distribution E(x, y) representing the outline of the differential image F(x, y); weight storage means 76b for storing in advance a weight distribution W(i, j); assessment value calculation means 75c for calculating an assessment value C(x, y) from the edge intensity distribution E(x, y) and the weight distribution W(i, j); and extraction means 76d for extracting object blood cells in the image F(x, y) based on the assessment value C(x, y).

Figure 4:
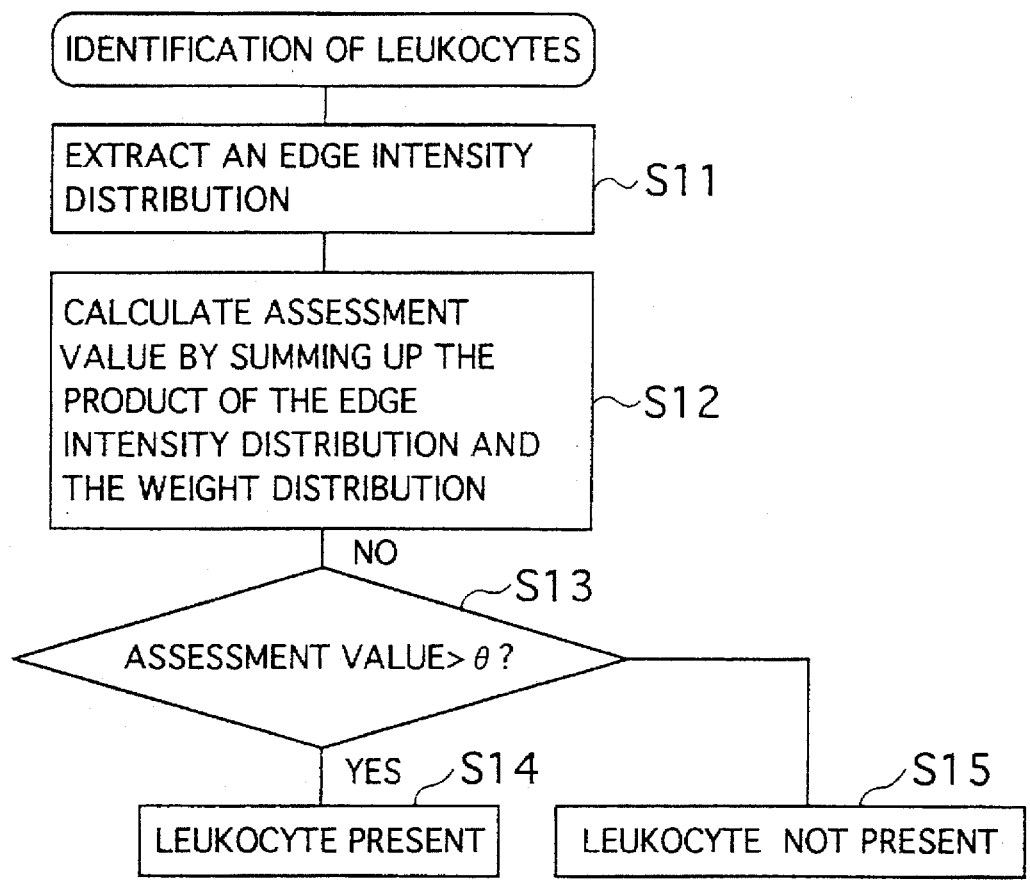
FIG. 4 is a flow chart for showing the operation of the embodiment of the present invention.

As shown in the flow chart of FIG. 4, the edge calculation means 76a calculates the edge intensity distribution E(x, y) in the step S11.

Figure 5:
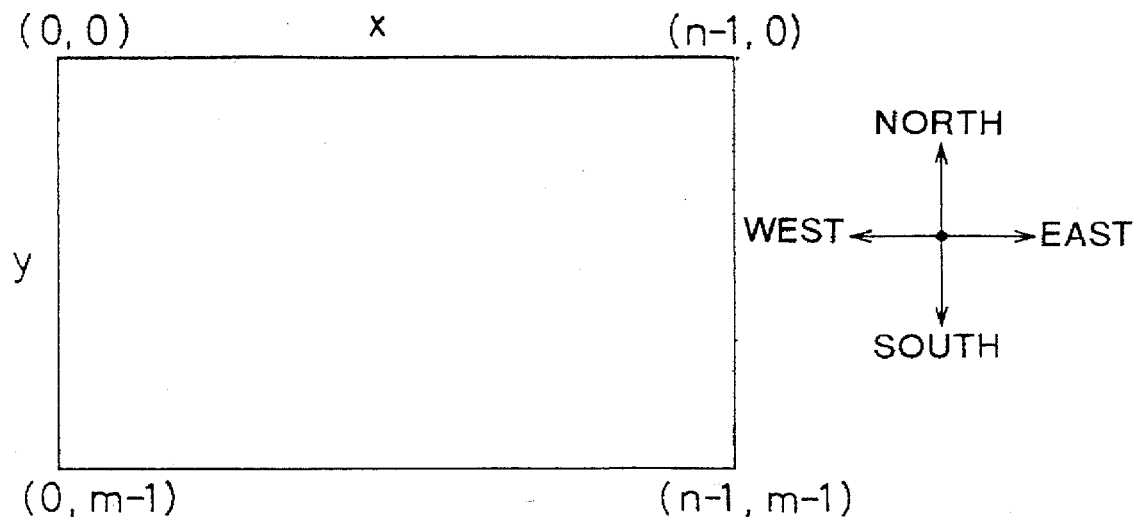
FIG. 5 is an explanatory view for defining the coordinates of the differential image according to the embodiment of the present invention.

The differential image F(x, y) is, assuming its size to be n×m pixels, represented by a two-dimensional coordinate plane ($0 \leq x \leq n-1$, $0 \leq y \leq m-1$) as shown in FIG. 5. A difference of pixel data between one pixel (x, y) and each of the four (or eight) neighboring pixels is calculated and, the edge intensity distribution E(x, y) at the pixel (x, y) is calculated by summing up the differences (step S11).

Figure 6:
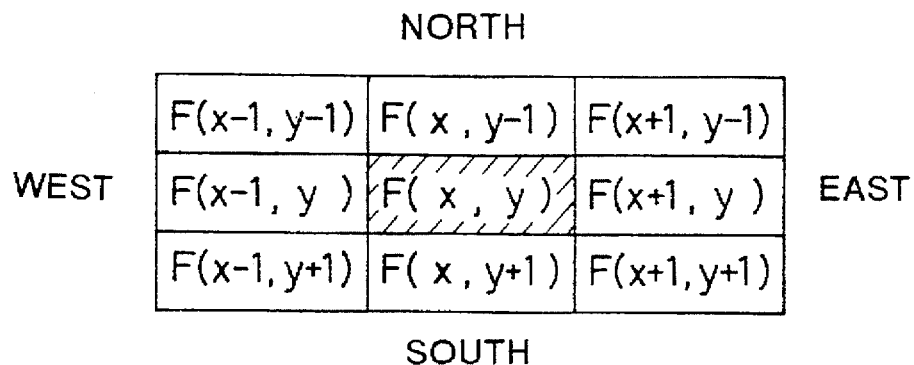
FIG. 6 is an explanatory view for showing image intensities of one pixel and its neighboring pixels according to the embodiment of the present invention.

In other words, since the pixel intensity of each of the neighboring pixels is represented as shown in FIG. 6, the edge intensity distribution E(x, y) will be determined by the following equation.

$$E(x, y) = |F(x, y)-F(x, y-1)| + |F(x, y)-F(x, y+1)| + |F(x, y)-F(x-1, y)| + |F(x, y)-F(x+1, y)| \quad (1)$$

Figure 7:
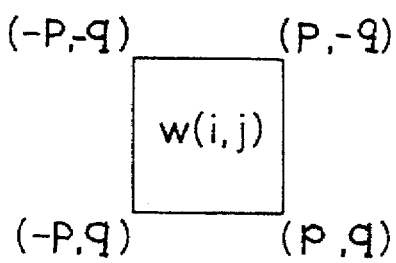
FIG. 7 is an explanatory view for defining the coordinates of the weight distribution according to the embodiment of the present invention.

Subsequently, the assessment value calculation means 76c calculates the assessment value C(x, y) at the pixel (x, y) as follows by using the weight distribution W(i, j) having a two-dimensional distribution as shown in FIG. 7 and stored in advance in the weight storage means 76b and the equation (1) (step S12).

$$C(x,y) = \sum_{i=-p}^{p} \sum_{j=-q}^{q} E(x+i, y+j) W(i,j) \qquad (2)$$

Here, it is assumed that the size of the weight distribution W(i, j) shown in FIG. 6 is (2p+1)×(2q+1) pixels and $-p \leq i \leq p$ and $-q \leq j \leq q$.

The extraction means 76d compares the assessment value C(x, y) with the threshold value e (step 818). If C(x, y) is greater than θ, it is inferred that a leukocyte is present at the pixel (x, y) (step St4). If not, it is inferred that a leukocyte is not present at the pixel (x, y) (step S18).

Thus, the leukocytes flowing through the center portion of the blood vessel at a fast flow rate and the leukocytes flowing along the blood vessel wall at a comparatively slow flow rate can be identified.

Figure 9:
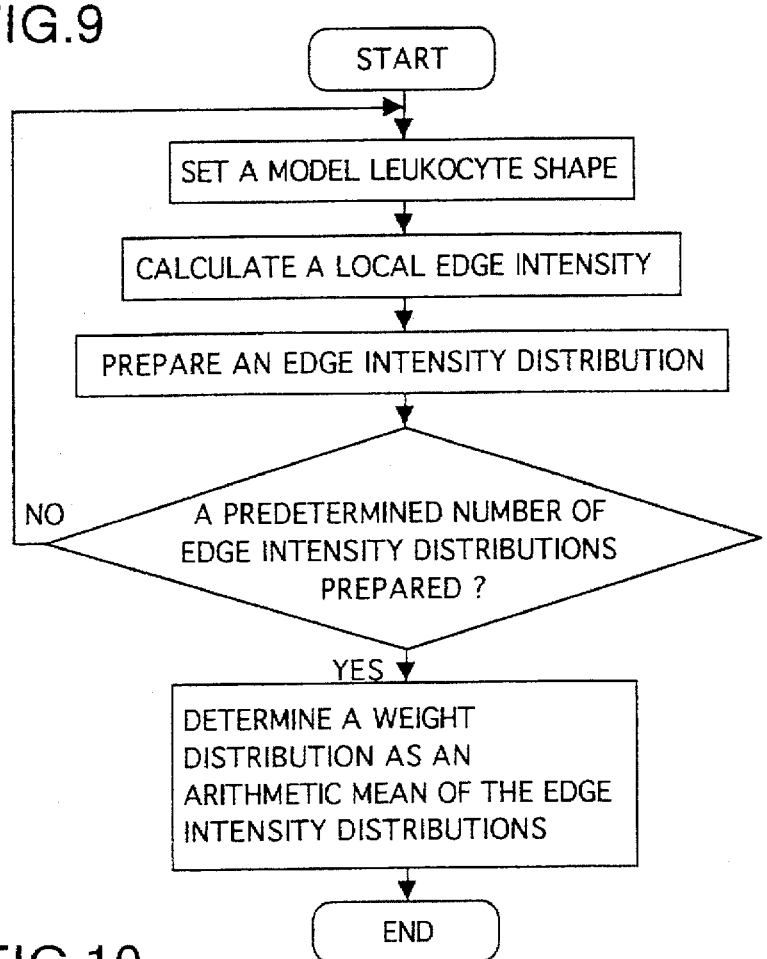
FIG. 9 is a flow chart for showing the steps in obtaining the weight distribution according to the embodiment of the present invention.

Here, the weight distribution W(i, j) used for the identification of leukocytes is determined as shown in the flow chart of FIG. 9.

Namely, the edges are extracted from the model leukocyte images having a shape varying little by little, and the weight distribution W(i, j) is determined as an arithmetic mean of the edge intensities.

Figure 10:
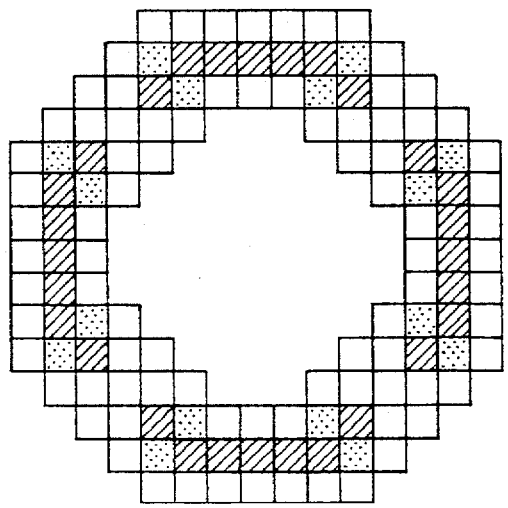
FIG. 10 is an explanatory view for showing an example of the weight distribution according to the embodiment of the present invention.

An example of the annular weight distribution W(i, j) thus determined is shown in FIG. 10. The weight distribution W(i, j) has weights of 1.0, 0.5, and 0.25.

The above calculation is carried out without taking the direction variance into consideration. However, by taking the direction variance into consideration, it is possible to prevent misidentification caused by body movement.

The four directions (north, south, east, and west) are taken into account in the x-y coordinate plane as shown in FIG. 5, and the edge intensity distribution E(x, y) with the direction variance taken into consideration is determined as follows with respect to each direction.

Namely, the edge intensity distribution $E_1$ (x, y) in the north direction, the edge intensity distribution $E_2$ (x, y) in the west direction, the edge intensity distribution $E_3$ (x, y) in the south direction, and the edge intensity distribution $E_4$ (x, y) in the east direction are determined as follows:

$$E_1(x,y) = \begin{cases} F(x,y) - F(x,y-1) & [F(x,y) \geq F(x,y-1)] \\ 0 & [F(x,y) < F(x,y-1)] \end{cases} \qquad (3)$$

$$E_2(x,y) = \begin{cases} F(x,y) - F(x-1,y) & [F(x,y) \geq F(x-1,y)] \\ 0 & [F(x,y) < F(x-1,y)] \end{cases} \qquad (4)$$

$$E_3(x,y) = \begin{cases} F(x,y) - F(x,y+1) & [F(x,y) \geq F(x,y+1)] \\ 0 & [F(x,y) < F(x,y+1)] \end{cases} \qquad (5)$$

$$E_4(x,y) = \begin{cases} F(x,y) - F(x+1,y) & [F(x,y) \geq F(x+1,y)] \\ 0 & [F(x,y) < F(x+1,y)] \end{cases} \qquad (6)$$

In this instance, the weight distribution W(i, j) shown in FIG. 10 is separated into the weight distributions $W_1$(i, j), $W_2$(i, j), $W_3$(x, y), and $W_4$(i, j) corresponding the four directions as shown in FIG. 11(a) to FIG. 11(d). Assessment values $C_1$(x, y), $C_2$(x, y), $C_3$(x, y), and $C_4$(x, y) are calculated with respect to the four directions from the equation (2). The calculated assessment values are summed up to yield C(x, y) which is compared with the threshold value for identification (recognition) of leukocytes. In this case, the weight distribution as shown in FIG. 11(a) to FIG. 11(d) have weights of 1.0, 0.5, 0.25, and 0.125.

The above calculation makes it possible to prevent the images generated by artifacts such as a noise from being misidentified as leukocytes.

Figure 21:
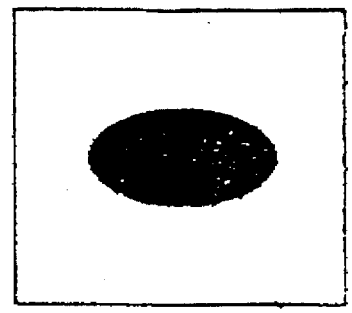
FIG. 21 is a view for showing an example of differential image of a leukocyte.
Figure 22:
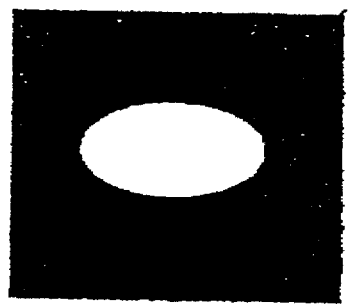
FIG. 22 is a view for showing an example of differential image created by artifacts.
Figure 23:
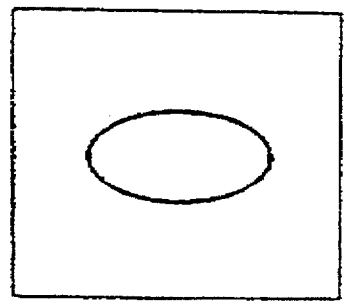
FIG. 23 is a view for showing an example of edge image corresponding to FIG. 21 and FIG. 22.

To be more specific, the edge intensity distribution obtained from a leukocyte shown in FIG. 21 and the edge intensity distribution obtained from an artifact caused by a noise shown in FIG. 22 are similar distributions as shown in FIG. 28. Accordingly, FIG. 22 will also be misidentified as a leukocyte if the edge distribution is calculated without taking the directions into consideration.

Figure 24:
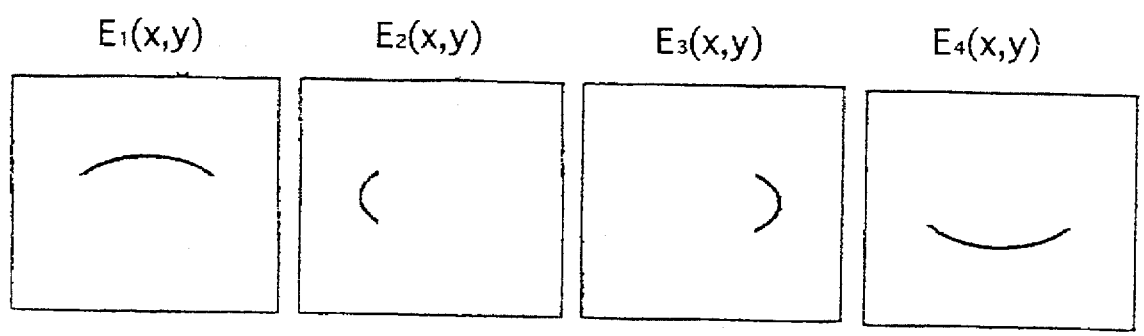
FIG. 24 is a view for showing an example of edge image corresponding to FIG. 21 when directions are taken into account.
Figure 25:
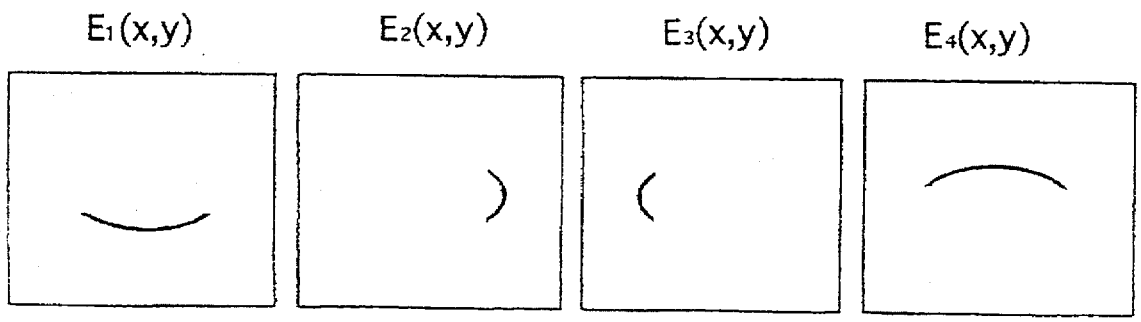
FIG. 25 is a view for showing an example of edge image corresponding to FIG. 22 when directions are taken into account.

However, when the directions are taken into consideration, the edge distributions will be as shown in FIG. 24 in the case of a leukocyte, whereas the edge distributions will be as shown in FIG. 25 in the case of an artifact. Here, black is represented by numeral "1" and white by "0" in FIG. 21 to FIG. 25.

Figure 11:
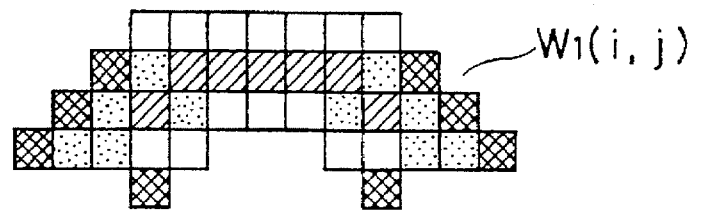
FIG. 11 is an explanatory view for showing another example of the weight distribution according to the embodiment of the present invention.
Figure 11:
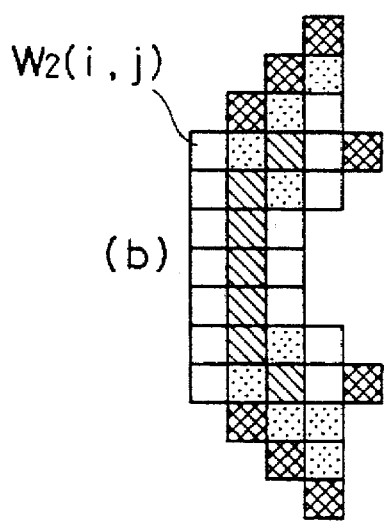
Figure 11:
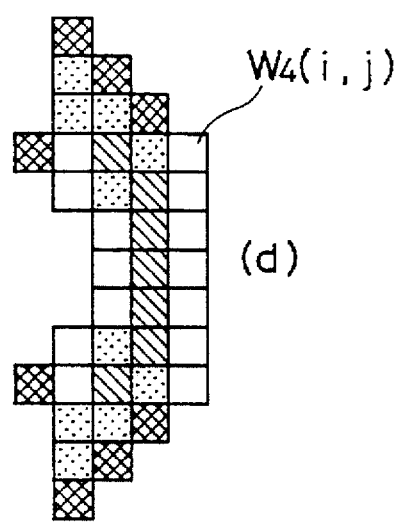
Figure 11:
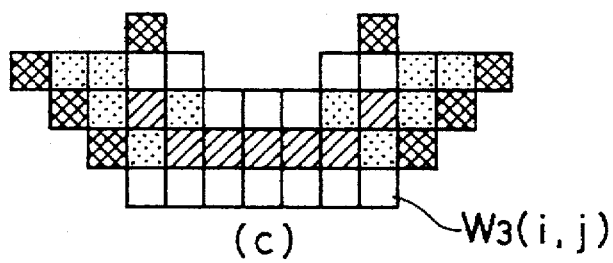
Figure 11:
Figure 11:
Figure 11:
Figure 11:

As a result of this, when a weight distribution such as shown in FIG. 11 is used, the assessment value C assumes a high value in the case of a leukocyte (FIG. 24), whereas the assessment value C assumes a value near 0 in the case of an artifact (FIG. 25), whereby the misidentification can be prevented.

Figure 12:
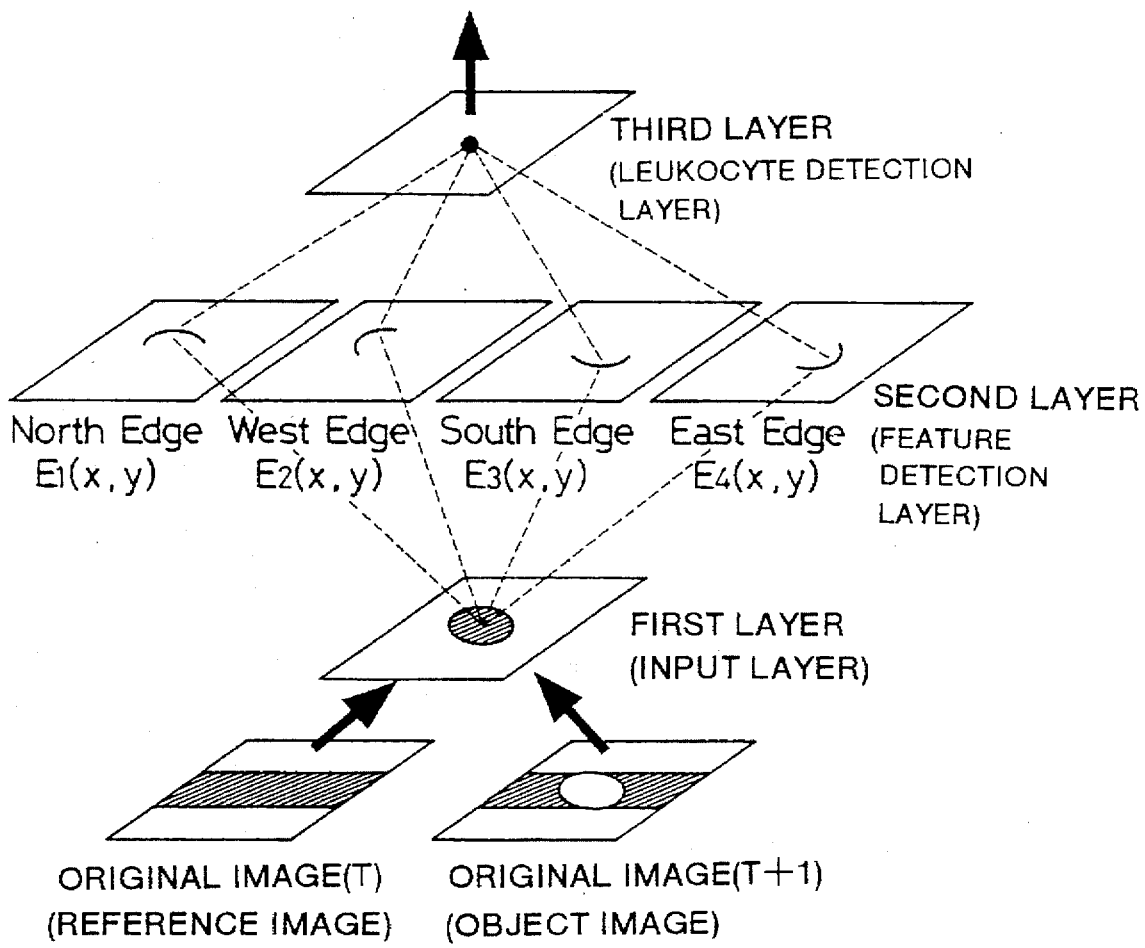
FIG. 12 is an explanatory view of the construction of a neural network applied to the embodiment of the present invention.

These artifacts are prone to be generated especially when a blur is created by body movement. In other words, when the blood vessel region is shifted during the period from the time t to the time (t+1), the shift (the blurring) may generate such artifacts Further, the digitizing means 75, the differential image forming means 72, and the image identification means 76 shown in FIG. 2 may also be equivalently constructed by utilizing a neural network In this instance, the neural network is constructed with a first layer (input layer), a second layer (feature detection layer), and a third layer (leukocyte detection layer) as shown in FIG. 12 and comprises n×m neurons in accordance with the image size shown in FIG. 4.

In the first layer, images at the time t and the time (t+1) are inputted and a difference thereof is outputted. The second layer is a feature extraction layer, wherein the differential image is inputted and the edges of the differential image with respect to the four directions are calculated and outputted by using the equations (3) to (6). The third layer is an identification layer, wherein a combination weight for combining the second layer with the third layer is determined independently or individually with respect to the four directions of the edge so that the third layer may catch fire when the position, direction, and intensity of the edge are found to be corresponding to a leukocyte.

In other words, the first layer corresponds to the differential image forming means 72, and the second and third layers correspond to the edge calculation means 76a, the weight storage means 76b, and the assessment value calculation means 76c, and the extraction means 76d.

The following is an explanation of the images obtained with the monitor television set 80 when leukocytes flowing through a capillary vessel in a nail wall of a human being are actually identified with the blood analyzing apparatus of the present invention.

FIG. 13 to FIG. 16 show images obtained when one leukocyte is identified, and FIG. 17 to FIG. 20 show images obtained when two leukocytes are identified.

Figure 13:
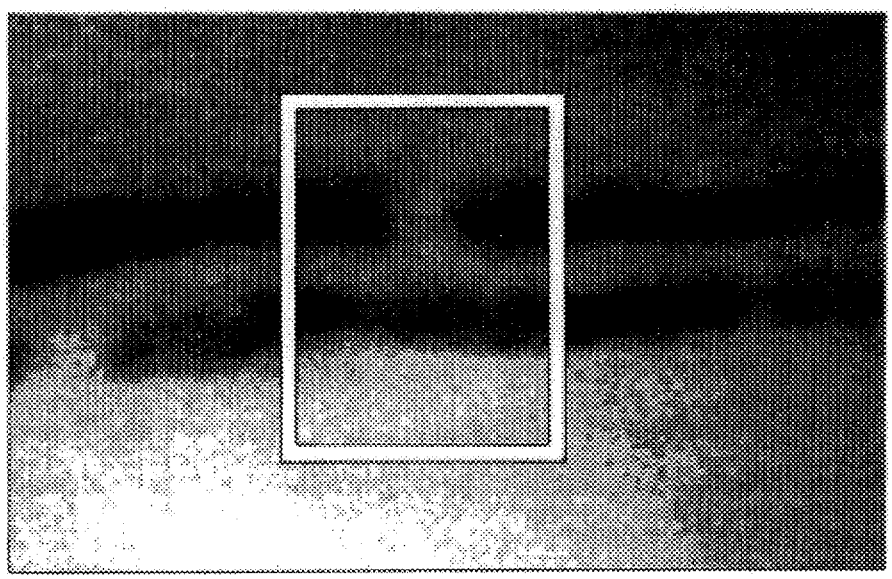
FIG. 13 is a view showing an example of original image obtained according to the embodiment of the present invention.
Figure 17:
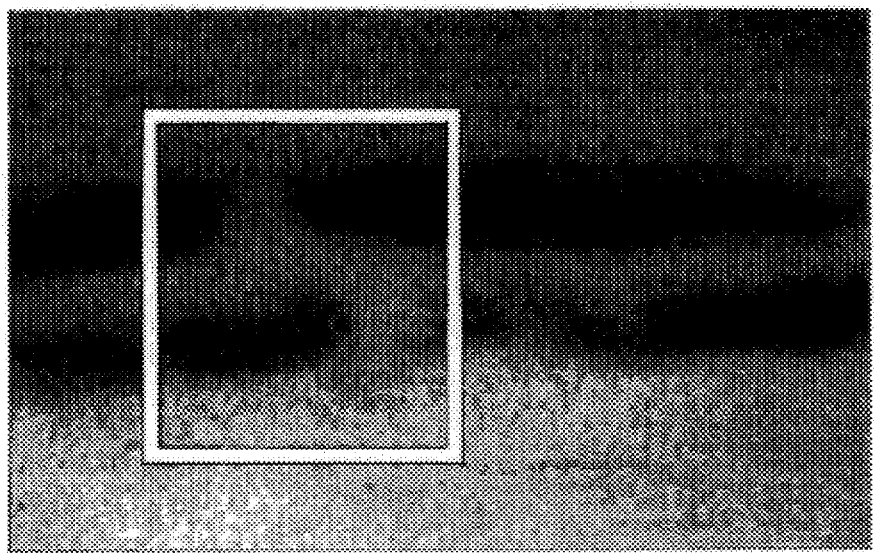
FIG. 17 is a view showing another example of original image obtained according to the embodiment of the present invention.

FIG. 13 shows an original image obtained at the time (t+1), in which the inside of the frame is a predetermined image region (an object image region) to be trimmed.

Figure 14:
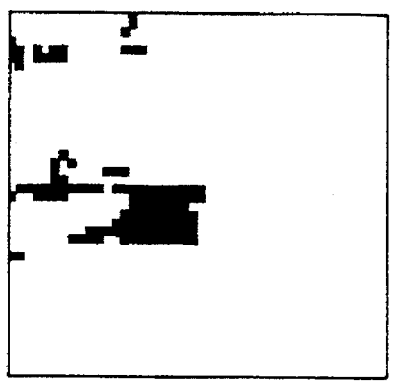
FIG. 14 is an explanatory view for showing an example of differential image obtained according to the embodiment of the present invention.

FIG. 14 shows a differential image obtained from a digitized object image of the predetermined region (inside of the frame) of FIG. 13 and a digitized reference image (not shown) obtained at the time t.

Figure 15:
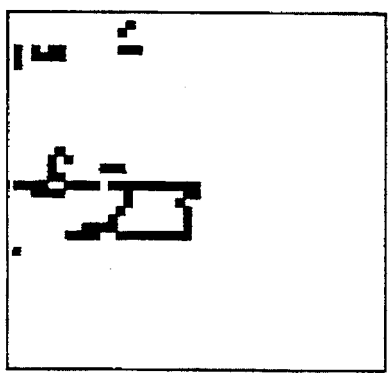
FIG. 15 is an explanatory view for showing an example of edge image obtained according to the embodiment of the present invention.
Figure 16:
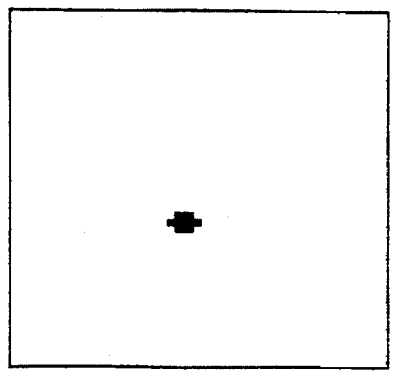
FIG. 16 is an explanatory view for showing the location of an identified leukocyte according to the embodiment of the present invention.
Figure 18:
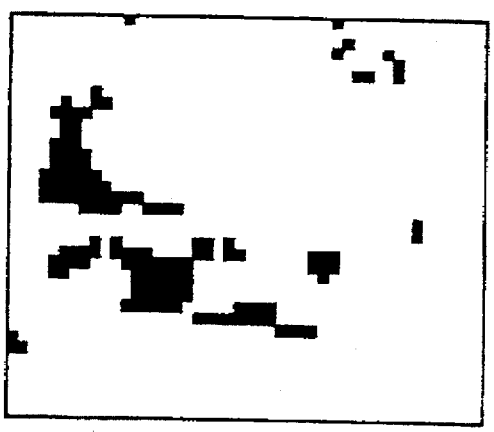
FIG. 18 is an explanatory view for showing another example of differential image obtained according to the embodiment of the present invention.
Figure 19:
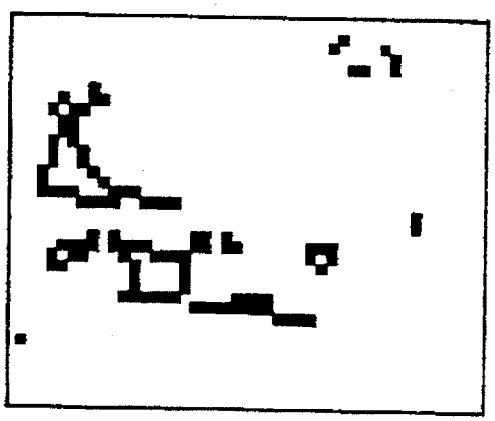
FIG. 19 is an explanatory view for showing another example of edge image obtained according to the embodiment of the present invention.
Figure 20:
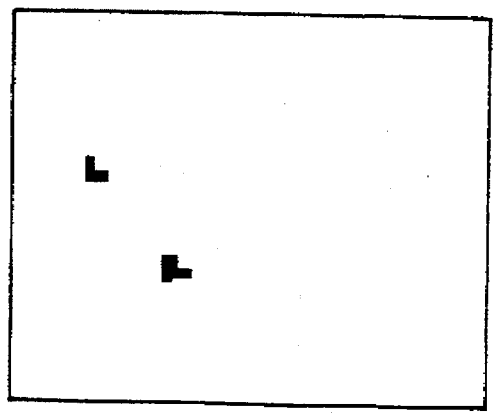
FIG. 20 is an explanatory view for showing the location of an identified leukocyte according to the embodiment of the present invention.

FIG. 15 shows an edge image namely the edge intensity distribution obtained from the differential image of FIG. 14. FIG. 16 shows an image indicating the position (the coordinates) of one extracted leukocyte. Here, black is represented by "1" and white by "0" in the images shown in FIG. 14 to FIG. 16.

FIGS. 17, 18, 19, and 20 correspond to FIGS. 13, 14, 15, and 16, respectively.

These figures show that the analyzing apparatus of the present invention identifies the presence of leukocytes accurately even if the leukocytes are greatly deformed in the blood vessel.

The present invention makes it possible to perform accurate and efficient identification of the object blood cells by weighting the edges of the leukocyte images in accordance with the model images of the object blood cells.

What we claim is:

1. An apparatus for analyzing blood including an image capturing device for capturing an image including at least one object blood cell and an analysis device for analyzing the captured image as an image $F(x, y)$ in an x-y coordinate system, the analysis device comprising:

edge calculation means for calculating an edge intensity distribution $E(x, y)$ representing an outline of the image $F(x, y)$;

weight storage means for prestoring a weight distribution $W(i, j)$ corresponding to an average outline of the at least one object blood cell;

assessment value calculation means for obtaining an assessment value $C(x, y)$ at each point $(x, y)$ by calculating a degree of correspondence between the edge intensity distribution $E(x, y)$ and the weight distribution $W(i, j)$ for each point $(x, y)$; and extraction means for extracting a point $(x, y)$ at which the assessment value $C(x, y)$ is larger than a predetermined value, thereby determining that the at least one object blood cell is present at the point $(x, y)$, so that the at least one object blood cell is identified.

2. An apparatus for analyzing blood according to claim 1, wherein the assessment value calculation means calculates the assessment value $C(x, y)$ at the point $(x, y)$ by the following equation:

$$C(x,y) = \sum_i \sum_j E(x+i, y+j) W(i,j)$$

where the right hand side of the above equation represents a sum of products of the edge intensity distribution and the weight distribution when the when both distributions are overlapped with each other so that the point $(x, y)$ in the edge intensity distribution corresponds to the point $(0, 0)$ in the weight distribution.

3. An apparatus for analyzing blood according to claim 1, wherein the weight distribution $W(i, j)$ is an annular distribution data corresponding to the outline of the object blood cells.

4. An apparatus for analyzing blood according to claim 1, wherein the edge calculation means calculates the edge intensity distributions $E1(x, y)$, $E2(x, y)$, . . . $En(x, y)$ corresponding to n different directions radiating from a point $(x, y)$, the weight storage means stores the weight distributions $W1(i, j)$, $W2(i, j)$, . . . $Wn(i, j)$ corresponding to the n different directions, and the assessment value calculation means calculates the assessment value by summing up the assessment values $C1(x, y)$, $C2(x, y)$, . . . $Cn(x, y)$ calculated corresponding to the n different directions.

5. An apparatus for analyzing blood according to claim 4, wherein each of the weight distributions $W1(i, j)$, $W2(i, j)$, . . . $Wn(i, j)$ is a portion of annular distribution data corresponding to the outline of the object blood cells.

6. An apparatus for analyzing blood according to claim 1, wherein the weight distribution $W(i, j)$ is calculated based on data obtained by summing up the edges extracted beforehand from a plurality of images of blood cells with the edge calculation means.

7. An apparatus for analyzing blood according to claim 1, wherein the image capturing device comprises an illuminator and an imaging device, the illuminator serving to illuminate a detection region including a blood vessel within a living body, and the imaging device serving to sequentially capture images of the illuminated detection region, and the analysis further comprises differential image creating means that creates a reference image using at least one of the sequentially captured images of the same detection region and, assuming another of the captured images to be an object image, creates a differential image by taking a difference between the object image and the reference image, whereby the image $F(x, y)$ is defined by the differential image.

8. An apparatus for analyzing blood according to claim 7, wherein the analysis device further comprises digitizing means for digitizing the reference image and the object image, whereby the differential image is defined by a difference between the digitized reference image and the digitized object image.

9. An apparatus for analyzing blood according to claim 1, wherein the analysis device comprises a neural network including the edge calculation means the weight storage means, the assessment value calculation means, and the extraction means.

10. An apparatus for analyzing blood according to claim 1, further comprising fixing means for relatively fixing a living body and the image capturing means so that the image capturing means is fixed on a surface of the living body corresponding to a desired detection region.

11. An apparatus for analyzing blood according to claim 1 further comprising calculation means for calculating the number of the object blood cells identified during a predetermined period of time when the image capturing device sequentially captures a plurality of images of a region including a blood vessel of a living body.

12. A method of analyzing blood using the apparatus of claim 1, the method comprising the steps of:

sequentially capturing a plurality of images of a region including a blood vessel of a living body, identifying object blood cells in the plurality of images, and calculating the number of per unit volume.

* * * * *